United States Patent
Burns

(10) Patent No.: US 12,005,472 B2
(45) Date of Patent: *Jun. 11, 2024

(54) VEE MANIFOLD

(71) Applicant: Rooftop Research, LLC, New Wilmington, PA (US)

(72) Inventor: Robert S. Burns, New Wilmington, PA (US)

(73) Assignee: Rooftop Research, LLC, New Wilmington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/804,282

(22) Filed: Feb. 28, 2020

(65) Prior Publication Data
US 2020/0197884 A1 Jun. 25, 2020

Related U.S. Application Data

(63) Continuation of application No. 14/968,030, filed on Dec. 14, 2015, now Pat. No. 10,610,837, which is a
(Continued)

(51) Int. Cl.
*B05C 17/005* (2006.01)
*A61B 17/00* (2006.01)
(Continued)

(52) U.S. Cl.
CPC ........ *B05C 17/00553* (2013.01); *B01F 25/40* (2022.01); *B01F 25/43141* (2022.01); *B01F 33/00* (2022.01); *B01F 33/50114* (2022.01); *B01F 35/12* (2022.01); *B05C 11/1002* (2013.01); *B05C 17/0052* (2013.01); *B67D 3/0058* (2013.01); *A61B 2017/00495* (2013.01);
(Continued)

(58) Field of Classification Search
CPC .... A61B 2017/00495; B05C 17/00553; B05C 17/0052; B01F 13/00; B01F 13/0027; B01F 5/06; B01F 5/0615; B01F 15/00038; Y10T 137/87161; Y10T 137/87153

See application file for complete search history.

(56) References Cited

U.S. PATENT DOCUMENTS 2,112,160 A 3/1938 Johnson
2,125,542 A 8/1938 Catterlin
(Continued)

FOREIGN PATENT DOCUMENTS

WO WO2010/095047 A2 8/2010

OTHER PUBLICATIONS

"Pipe Thread Basics" by Huyett publicly available since Feb. 2021 (Year: 2021).*

*Primary Examiner* — David Colon-Morales
(74) *Attorney, Agent, or Firm* — Dority & Manning, P.A.

(57) ABSTRACT

A manifold having a first side, a second side, a first channel extending from the first side to the second side, and a second channel extending from the first side to the second side is disclosed. The first channel and the second channel each define a linear longitudinal axis. In one embodiment, the first channel longitudinal axis and the second channel longitudinal axis are oblique to the first side and the second side of the manifold. The manifold of the present disclosure provides channels that can be easily cleaned and allow for an increased flow performance.

20 Claims, 7 Drawing Sheets

US 12,005,472 B2

Page 2

Related U.S. Application Data continuation of application No. 13/804,748, filed on Mar. 14, 2013, now Pat. No. 9,242,846.

(60) Provisional application No. 61/623,610, filed on Apr. 13, 2012.

(51) Int. Cl.
  *B01F 25/40* (2022.01)
  *B01F 25/4314* (2022.01)
  *B01F 33/00* (2022.01)
  *B01F 33/501* (2022.01)
  *B01F 35/12* (2022.01)
  *B05C 11/10* (2006.01)
  *B67D 3/00* (2006.01)

(52) U.S. Cl.
  CPC ............... *Y10T 137/87153* (2015.04); *Y10T 137/87161* (2015.04)

(56) References Cited

U.S. PATENT DOCUMENTS

| | | | |
|---|---|---|---|
| 3,223,083 A | 12/1965 | Cobey | |
| 3,390,814 A | 7/1968 | Creighton, Jr. et al. | |
| 3,884,388 A | 5/1975 | Holcomb | |
| 4,121,739 A | 10/1978 | Devaney et al. | |
| 4,506,665 A | 5/1985 | Andrews et al. | |
| 4,557,261 A | 12/1985 | Reugheimer | |
| 4,852,387 A | 8/1989 | Bingham | |
| 4,852,563 A | 8/1989 | Gross | |
| 4,979,942 A | 12/1990 | Wolf et al. | |
| 5,104,375 A | 4/1992 | Wolf et al. | |
| 5,116,315 A | 5/1992 | Capozzi et al. | |
| 5,309,906 A | 5/1994 | LaBombard | |
| 5,324,274 A | 6/1994 | Martin | |
| 5,344,074 A | 9/1994 | Spriggs et al. | |
| 5,443,183 A | 8/1995 | Jacobsen et al. | |
| 5,474,540 A | 12/1995 | Miller et al. | |
| 5,558,124 A | 9/1996 | Randall | |
| 5,575,767 A | 11/1996 | Stevens | |
| 5,582,596 A | 12/1996 | Fukunaga et al. | |
| 5,665,067 A | 9/1997 | Linder et al. | |
| 5,676,280 A | 10/1997 | Robinson | |
| 5,887,755 A | 5/1999 | Hood, III | |
| 6,047,729 A | 4/2000 | Hollister et al. | |
| 6,132,396 A | 10/2000 | Antanavich et al. | |
| 6,161,730 A | 12/2000 | Heusser et al. | |
| 6,202,698 B1 | 5/2001 | Stearns | |
| 6,527,749 B1 | 3/2003 | Roby et al. | |
| 6,764,026 B2 | 7/2004 | Hunter et al. | |
| 6,811,096 B2 | 11/2004 | Frazier et al. | |
| 6,832,621 B1 | 12/2004 | Williams | |
| 6,936,033 B2 | 8/2005 | McIntosh et al. | |
| 6,994,686 B2 | 2/2006 | Cruise et al. | |
| 7,037,694 B2 | 5/2006 | Aksenov et al. | |
| 7,290,541 B2 | 11/2007 | Ivri et al. | |
| 7,641,075 B2 | 1/2010 | Crews | |
| 8,088,099 B2 | 1/2012 | McIntosh et al. | |
| 8,152,777 B2 | 4/2012 | Campbell et al. | |
| 9,242,846 B2 * | 1/2016 | Burns | B67D 3/0058 |
| 10,610,837 B2 * | 4/2020 | Burns | B05C 11/1002 |
| 2003/0069537 A1 * | 4/2003 | Spero | A61B 17/00491 604/82 |
| 2003/0191496 A1 * | 10/2003 | Edwards | A61B 17/0057 606/213 |
| 2003/0209612 A1 | 11/2003 | Hahnen | |
| 2007/0187434 A1 | 8/2007 | Schrafel | |
| 2008/0144426 A1 | 6/2008 | Janssen et al. | |
| 2009/0038701 A1 | 2/2009 | Delmotte | |
| 2009/0108091 A1 | 4/2009 | Steffen | |
| 2009/0266918 A1 | 10/2009 | Fortier et al. | |
| 2010/0249829 A1 * | 9/2010 | Rissman | A61B 17/00491 606/213 |
| 2011/0092899 A1 * | 4/2011 | Ohri | A61B 17/00491 604/82 |
| 2011/0268845 A1 | 11/2011 | Fantappie | |
| 2011/0282381 A1 * | 11/2011 | Cronin | A61M 5/1407 606/213 |
| 2012/0035335 A1 | 2/2012 | Ladet et al. | |
| 2012/0292343 A1 | 11/2012 | Zimmerman et al. | |
| 2020/0062574 A1 * | 2/2020 | Burns | E04D 15/07 |
| 2020/0246816 A1 * | 8/2020 | Burns | B05B 7/2472 |
| 2023/0086665 A1 * | 3/2023 | Burns | B67D 3/0058 |

\* cited by examiner

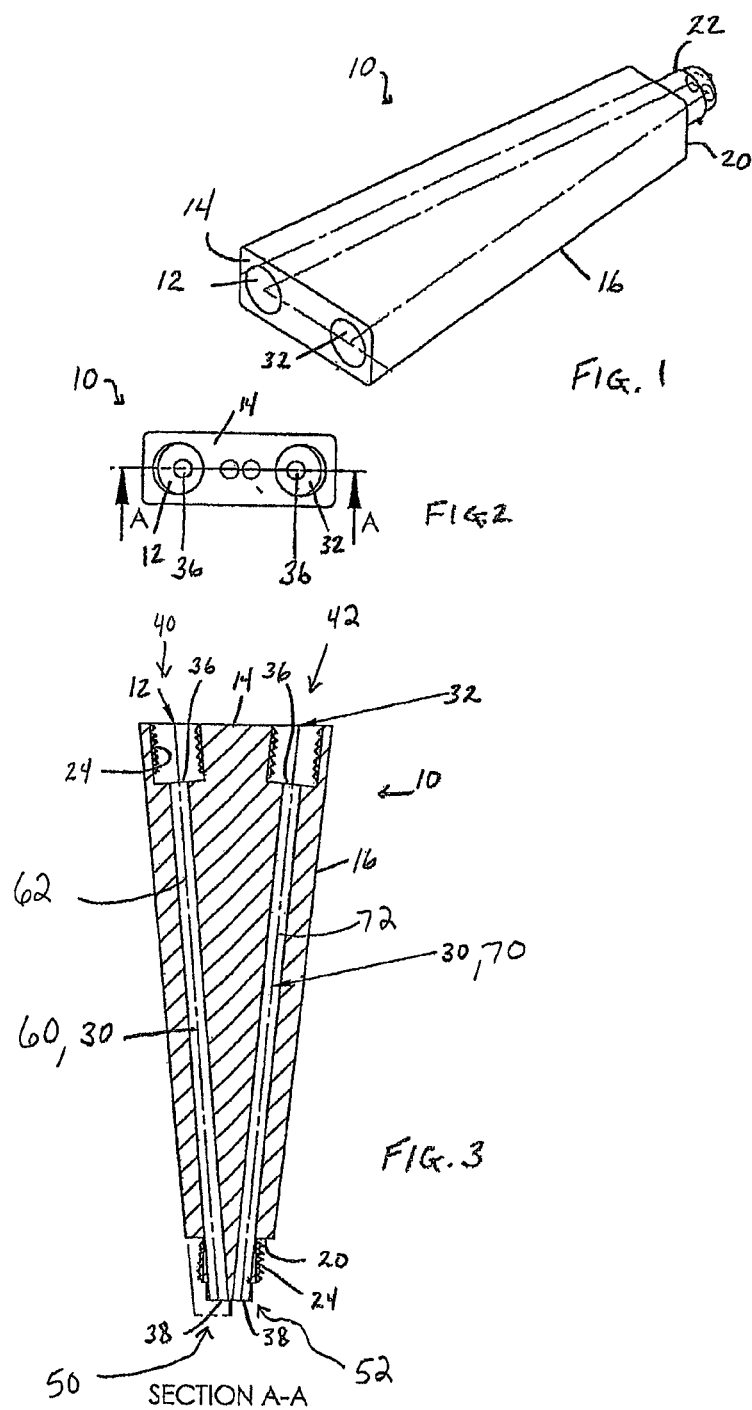

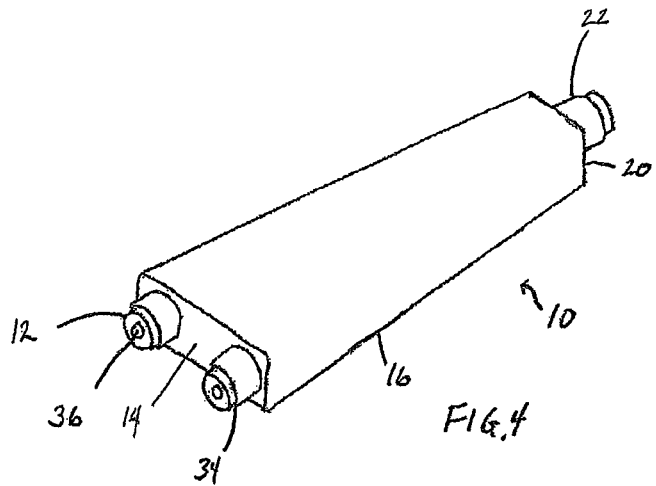
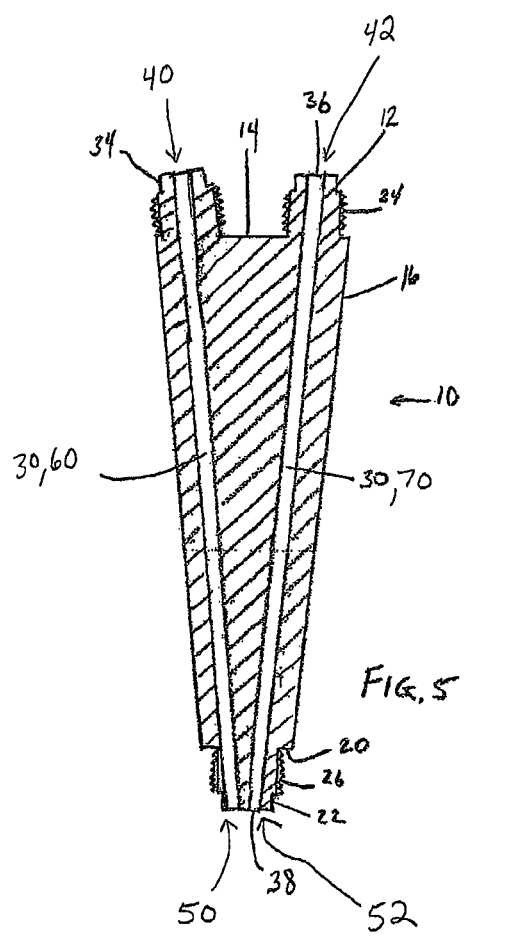
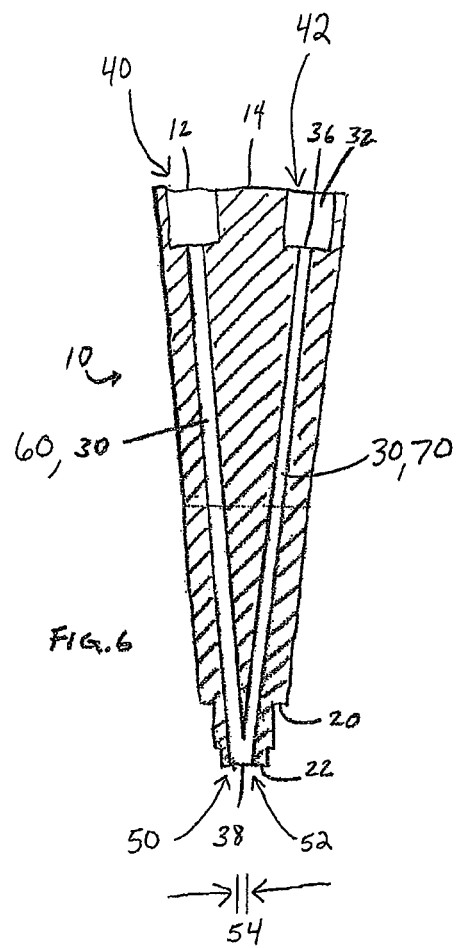

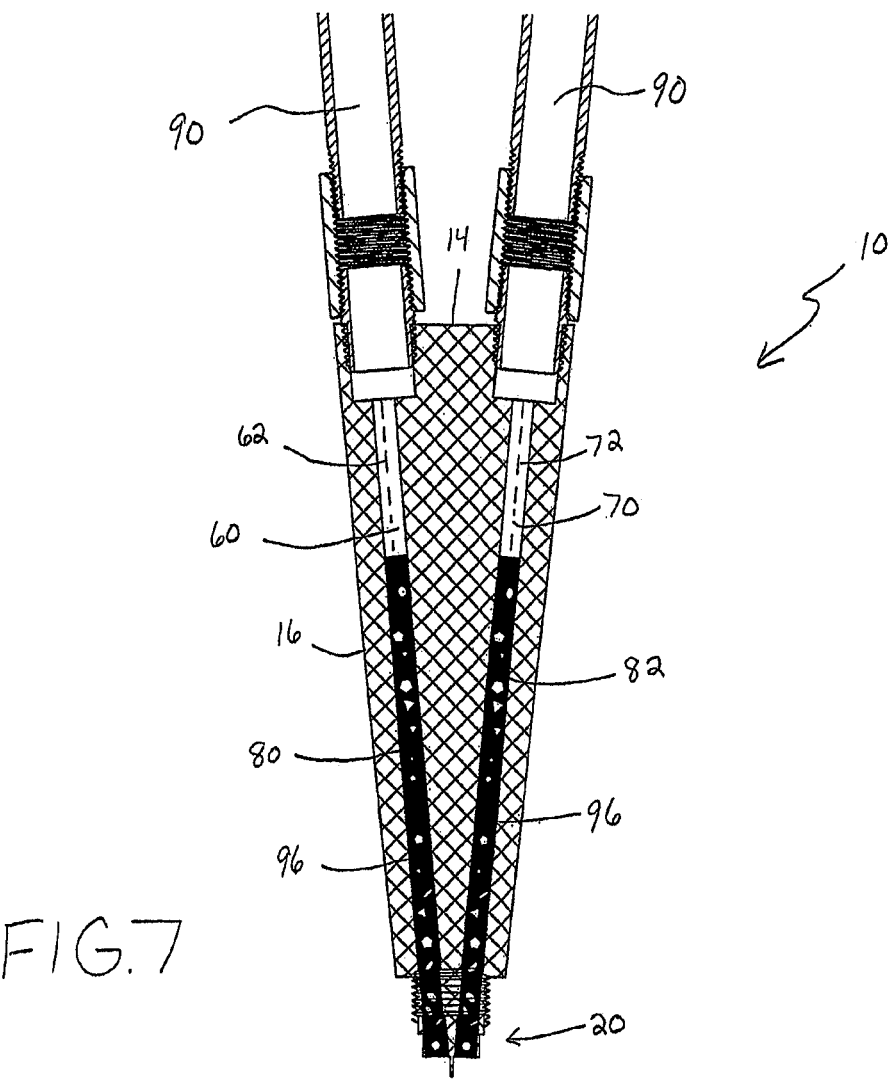
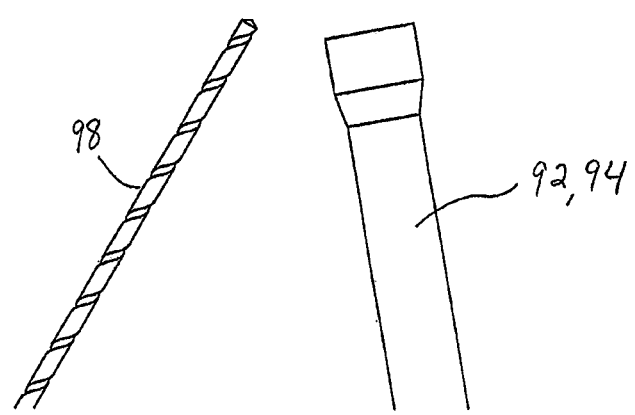
FIG. 7

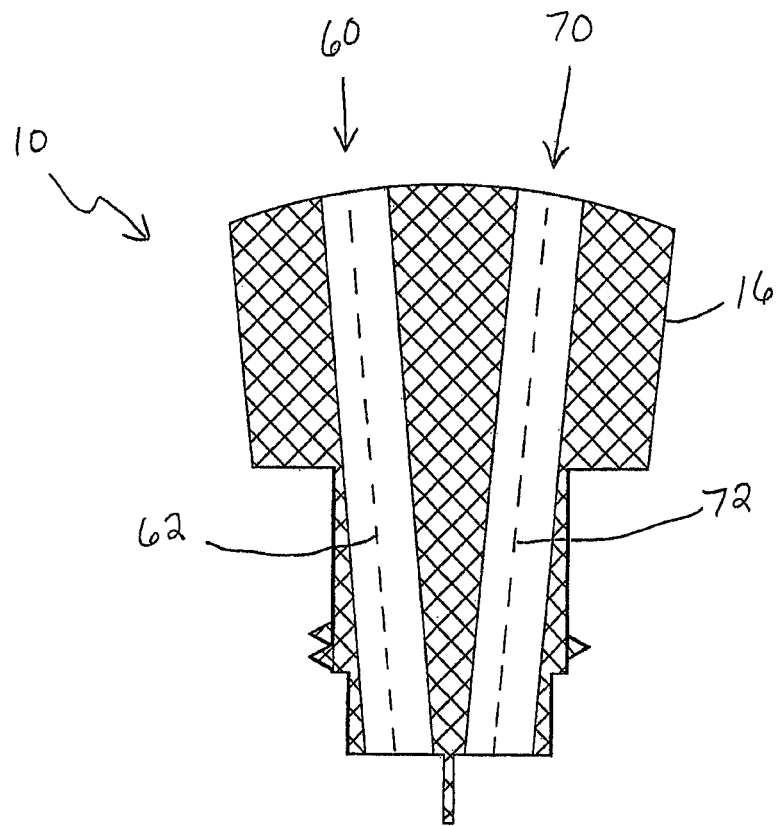
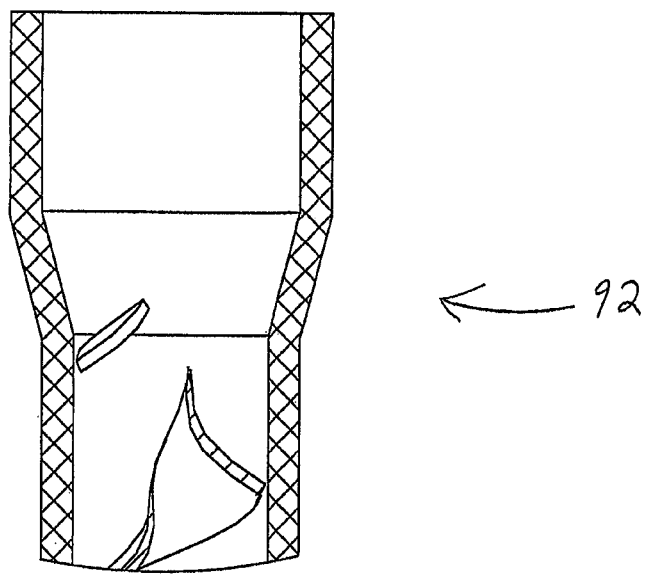
FIG. 8B

VEE MANIFOLD

CROSS-REFERENCE TO RELATED APPLICATIONS

The present application is a continuation of and claims priority to U.S. application Ser. No. 14/968,030 entitled "Vee Manifold", filed Dec. 14, 2015, which claims priority to U.S. application Ser. No. 13/804,748 entitled "Vee Manifold", filed Mar. 14, 2013, which claims priority to U.S. Provisional Patent Application No. 61/623,610, filed Apr. 13, 2012, the entire disclosures of which are hereby expressly incorporated by reference herein.

BACKGROUND OF THE INVENTION

1. Field of the Disclosure

The present invention relates to an improved manifold for dispensing of multiple component adhesives and other liquids. More particularly, the present invention provides an improved manifold that is easily cleanable.

2. Description of the Related Art

The delivery of liquid materials through tubing, hoses, or pipes is simple and well known. Differing materials traveling concurrently through separate tubes are also common. It is frequently desirable for differing materials traveling through multiple tubes to converge into one tube. As liquids flow towards this point of convergence, the contour of the tube path will impact the flow performance of the liquid, increase or decrease the frictional resistance of the liquid, and affect the ease with which the tubes can be maintained, cleaned or unclogged.

The joining of multiple liquids requires a special tubing manifold such as a wye manifold. The design of the adapter is critical to liquid delivery performance. This apparatus is particularly important when used by an operator to apply a multiple component liquid such as a coating or an adhesive to a surface.

The wye manifold derives its name from the fact that it has a generally Y-shaped body or housing when it is configured to interconnect two upper tubular strings ("chemical feed tubes") to a single lower tubular string ("discharge tube"). As used herein, the term "wye manifold" includes configurations in which two or more chemical hoses are interconnected to another discharge tube by the wye manifold body or housing.

A prior art dual manifold, as illustrated in FIG. 5 of U.S. patent application publication 2012/0012054 A1 is used to apply two-part adhesives utilizing a wye manifold wherein the shape of an internal path is constructed with 90 degree angles as parallel first paths. The 90 degree angled paths are created from partially drilling faces of the wye manifold and connecting with a perpendicular path. Such prior art wye manifolds have flow paths with angles which require increased pressure for use.

In addition, when wye manifolds clog due to chemical reaction or physical change of the materials within, cleaning is not readily accomplished by applying pressure or by drilling due to the configuration of the internal pathways and the angles at which they are disposed within the manifold. Wye manifolds are often utilized for the purpose of merging the flow path of liquids. The merging of liquids frequently causes a chemical reaction with many multiple component coatings and adhesives. When the stream of materials is stopped or slowed, the chemicals begin to react right at this merge point. Often the curing of these liquids begins at the merge point and then progresses upstream past the angle change and up into the inlets of the wye manifold. The curing process results in clogging as the physical state changes from that of a liquid to a solid or gel. The resulting hardened mass takes on the shape of the wye. The inside walls of the wye manifold act like a mold while the materials set up and cure. This hardened mass could be forcibly moved downstream and out of the wye manifold if the shape of the tubing were straight. But the change in the angle of the flow path molds this mass into a shape with an elbow. This elbow of the mass is now locked into place by the angled elbow of the wye manifolds. If pressure is applied in an attempt to dislodge this clog, the hardened mass cannot flow past the corner and the wye manifold is clogged. It is not possible to eject this hardened mass by increasing the pressure of the fluids.

Restoring this wye manifold into a usable part is normally accomplished with mechanical means. A drill bit can be inserted into the outlet of wye. The spinning drill bit will remove the clogged mass from the lower part of the wye outlet. In order to access this opening, the downstream plumbing must be removed. Examples of downstream plumbing are spray nozzles and static mixing tips. In order to access the inlets of the wye manifolds, the liquid supply lines must also be removed. Cleaning out the manifold requires not only drilling up from the outlet and down through the inlet, but also a side plug must be removed to allow the drill to be inserted to clean out the horizontal portion of the clogged path. At that point, the drill bit can be inserted into each opening to clear out the hardened mass clog. This process is not only time consuming but extremely messy, expensive, and wasteful as the liquid in the supply lines usually flows out and cannot be recovered.

For overnight storage, the flow path of the wye manifold must be purged to prevent hardening of the materials. Additionally, it is often recommended that the outlets be filled with grease to prevent hardening. This shut down procedure at the end of each use is quite time consuming and the grease has to be purged prior to the next start up.

In view of the foregoing, it will be appreciated that a need exists for an improved manifold in which multiple chemical feed tubes are interconnected.

SUMMARY OF THE INVENTION

The present disclosure provides a manifold having a first side, a second side, a first channel extending from the first side to the second side, and a second channel extending from the first side to the second side. The first channel and the second channel each define a linear longitudinal axis. In one embodiment, the first channel longitudinal axis and the second channel longitudinal axis are oblique to the first side and the second side of the manifold. The manifold of the present disclosure provides channels that can be easily cleaned. For example, the channels can be cleaned by increasing a pressure of a substance traveling through the manifold. Also, the channels can be cleaned using a tool having a linear longitudinal axis, wherein the tool only needs to be inserted into each channel one time.

The manifold of the present disclosure is compatible with the limited spaces provided by plumbing components, such as a static mixing tip, which are attachable to an end of the manifold. For example, when multiple paths of dissimilar materials travel through hoses and arrive at a manifold, the purpose of the manifold is to direct the material flows toward each other so that they can be mixed together. The connecting apparatuses, such as a spray nozzles or static mixing tips, are commercially established in limited sizes.

In accordance with an embodiment of the present disclosure, a manifold, for a first substance and a second substance to travel therethrough, includes a block having a first side and a second side, the first side of the block defining a first side first aperture and a first side second aperture, the first side second aperture spaced a first distance from the first side first aperture, the second side of the block defining a second side first aperture and a second side second aperture. The manifold includes a first channel extending from the first side first aperture to the second side first aperture, the first channel defining a first channel longitudinal axis, the first channel longitudinal axis being linear, and a second channel extending from the first side second aperture to the second side second aperture, the second channel defining a second channel longitudinal axis, the second channel longitudinal axis being linear, wherein the first substance is movable through the first channel and the second substance is movable through the second channel.

In one configuration, the first channel longitudinal axis is oblique to the first side and the second side of the block. In another configuration, the second channel longitudinal axis is oblique to the first side and the second side of the block. In yet another configuration, the second side second aperture is spaced a second distance from the second side first aperture. In one configuration, the first distance is greater than the second distance. In another configuration, the first substance and the second substance are different. In yet another configuration, the manifold is attachable to a static mixing tip. In another configuration, the manifold is attachable to a spray nozzle.

A first aspect in accordance with another embodiment of the present disclosure is a vee manifold for delivering a plurality of materials. The vee manifold comprises a block having a plurality of inlets on a first side, each inlet comprises a first attachment means. The block also has an outlet portion on a second side opposite the first side. The outlet portion comprises a second attachment means. The block further comprises a plurality of generally straight, generally cylindrical channels between the plurality of inlets and the outlet portion forming a flow path from the inlets to the outlet portion.

In preferred embodiments, the first attachment means are female attachment means and the second attachment means is a male attachment means. In preferred embodiments, the second attachment means are quick connect fittings. In more preferred embodiments, the first attachment means is threading. In still more preferred embodiments, the second attachment means is threading.

A second aspect in accordance with another embodiment of the present disclosure is a vee manifold for delivering a plurality of materials comprising a block having a male attachment means having an outer end surface and screw threads on a side surface, the block having a plurality of female screw attachment means each having a recessed end surface and screw threads on a female side surface; and the block defining individual, open cylindrical channels between each of the plurality of recessed end surfaces and the outer end surface. In preferred embodiments, the axes of the cylindrical channels intersect outside the block and outside the male attachment means. The outlets of the cylindrical channels are contained within the male attachment means. In other preferred embodiments, axes of the cylindrical channels intersect at the outer end surface.

Both aspects share some preferred embodiments. Preferred embodiments are comprised of a polymer. More preferred embodiments are comprised of ultra-high-molecular weight polyethylene. Preferred embodiments of either aspect comprise two cylindrical channels. More preferred embodiments are where the cylindrical channels are non-intersecting. Yet more preferred embodiments are where axes of the cylindrical channels intersect at the surface of the vee manifold. Yet more preferred embodiments are where axes of the cylindrical channels intersect outside the vee manifold. In still other preferred embodiments, the cylindrical channels have similar cross sectional areas. In some preferred embodiments of either aspect; the vee manifold has heating means.

In accordance with another embodiment of the present disclosure, a manifold for a first substance and a second substance to travel therethrough includes a block having a first side and a second side, the block having a vee-shape; a first channel extending from the first side to the second side, the first channel defining a first channel longitudinal axis, the first channel longitudinal axis being linear; and a second channel extending from the first side to the second side, the second channel defining a second channel longitudinal axis, the second channel longitudinal axis being linear, wherein the first channel and the second channel are inclined toward each other as the first channel and the second channel extend from the first side of the block to the second side of the block, and wherein the first channel and the second channel together form a vee-shape.

In one configuration, the block has a stepped surface adjacent the second side. In another configuration, the first side of the block has a first width and the second side of the block has a second width, the first width greater than the second width. In yet another configuration, the first channel has a uniform diameter. In one configuration, the second channel has a uniform diameter. In another configuration, the first channel and the second channel intersect at a point outside of the block. In yet another configuration, the manifold includes a first connection portion disposed at a first portion of the first side of the block; a second connection portion disposed at a second portion of the first side of the block; and a third connection portion disposed at a third portion of the second side of the block.

In accordance with another embodiment of the present disclosure, a manifold for a first substance and a second substance to travel therethrough includes a block having a first side and a second side, the block having a vee-shape; a first channel extending from the first side to the second side, the first channel defining a first channel longitudinal axis, the first channel longitudinal axis being linear; and a second channel extending from the first side to the second side, the second channel defining a second channel longitudinal axis, the second channel longitudinal axis being linear, wherein the first channel and the second channel are inclined toward each other as the first channel and the second channel extend from the first side of the block to the second side of the block, wherein the first channel and the second channel together form a vee-shape, and wherein the block has a stepped surface adjacent the second side.

In one configuration, the first side of the block has a first width and the second side of the block has a second width, the first width greater than the second width. In another configuration, the first channel has a uniform diameter. In yet another configuration, the second channel has a uniform diameter. In one configuration, the first channel and the second channel intersect at a point outside of the block. In another configuration, the manifold includes a first connection portion disposed at a first portion of the first side of the block; a second connection portion disposed at a second portion of the first side of the block; and a third connection portion disposed at a third portion of the second side of the block.

In accordance with another embodiment of the present disclosure, a manifold for a first substance and a second substance to travel therethrough includes a block having a first side and a second side, the block having a vee-shape; a first channel extending from the first side to the second side, the first channel defining a first channel longitudinal axis, the first channel longitudinal axis being linear, the first channel having a uniform diameter; and a second channel extending from the first side to the second side, the second channel defining a second channel longitudinal axis, the second channel longitudinal axis being linear, the second channel having a uniform diameter, wherein the first channel and the second channel are inclined toward each other as the first channel and the second channel extend from the first side of the block to the second side of the block, wherein the first channel and the second channel together form a vee-shape, and wherein the block has a stepped surface adjacent the second side.

These and other advantages of the invention will be appreciated by reference to the detailed description of the preferred embodiment(s) that follow.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1 is a perspective view of a first embodiment of the vee manifold of the present invention.

FIG. 2 is a first end view of the embodiment of the vee manifold of FIG. 1.

FIG. 3 is a cross-sectional view of an embodiment of the vee manifold.

FIG. 4 is a perspective view of an embodiment of the vee manifold of the present invention.

FIG. 5 is a cross-sectional view of an embodiment of the vee manifold.

FIG. 6 is a cross-sectional view of another embodiment of the vee manifold.

FIG. 7 is another cross-sectional view of another embodiment of the vee manifold.

FIG. 8B is an enlarged, partial cross-sectional view of the vee manifold and the static mixing tip of FIG. 8A taken along section 8B.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

In the following detailed description, reference is made to the accompanying examples and figures that form a part hereof, and in which is shown, by way of illustration, specific embodiments in which the inventive subject matter may be practiced. These embodiments are described in sufficient detail to enable those skilled in the art to practice them, and it is to be understood that other embodiments may be utilized and that structural or logical, changes may be made without departing from the scope of the inventive subject matter. Such embodiments of the inventive subject matter may be referred to, individually and/or collectively, herein by the term "invention" merely for convenience and without intending to voluntarily limit the scope of this application to any single invention or inventive concept if more than one is in fact disclosed. The following description is, therefore, not to be taken in a limited sense, and the scope of the inventive subject matter is defined by the appended claims and their equivalents.

In the following description of the apparatus and methods described herein, directional terms, such as "top", "bottom", "upstream", "downstream", etc., are used for convenience in referring to the accompanying drawings. Additionally, it is to be understood that the various embodiments of the present invention described herein may be utilized in various orientations, such as inclined, inverted, horizontal, vertical, etc., without departing from the principles of the present invention. Typical material flow is from upstream to downstream.

Representatively illustrated in FIGS. 1-6 is an apparatus of a vee manifold 10 which apparatus embodies principles of the present invention. The vee manifold 10 offers a uniquely designed apparatus that provides for increased flow performance, at a reduced pressure, and a flow path that is easily maintained as compared to prior art wye manifolds.

Figure 8A:
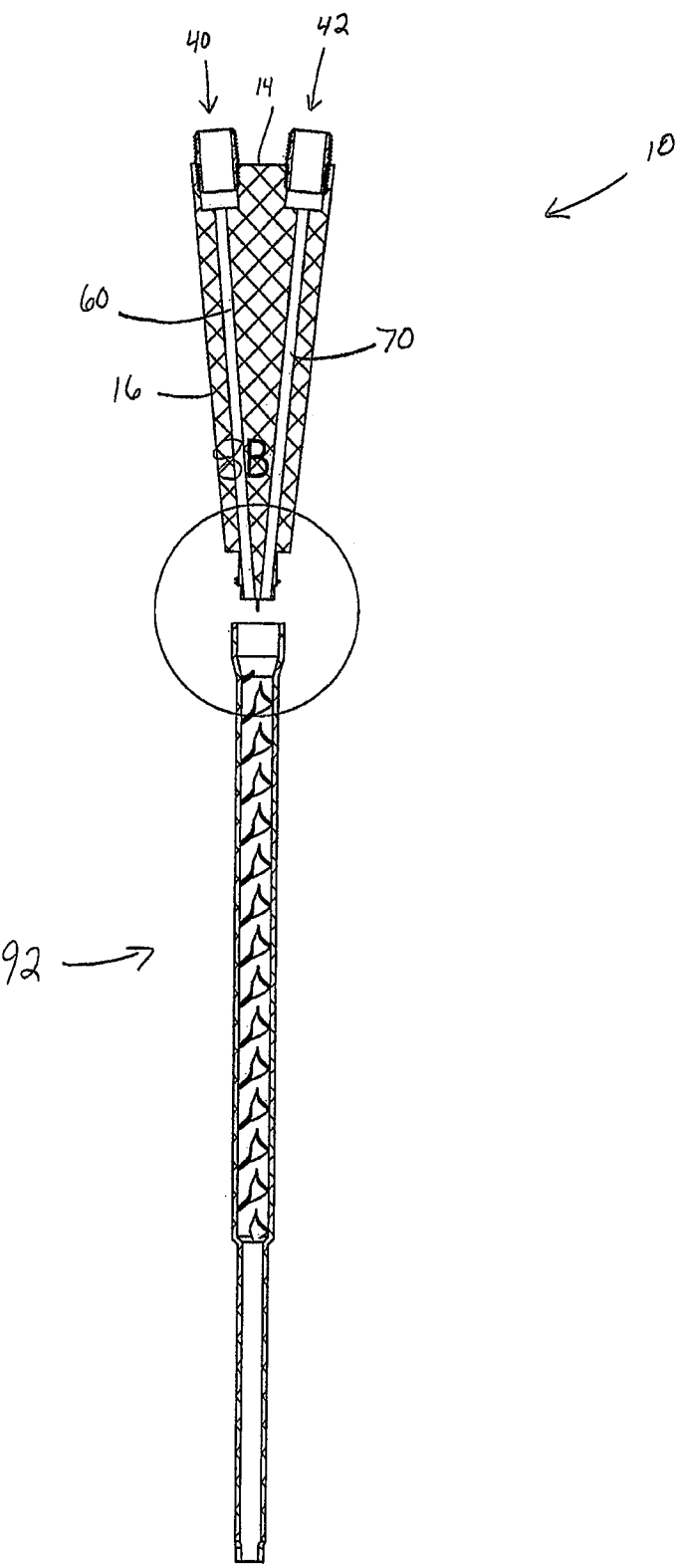
FIG. 8A is another cross-sectional view of another embodiment of the vee manifold with a static mixing tip.
Figure 9:
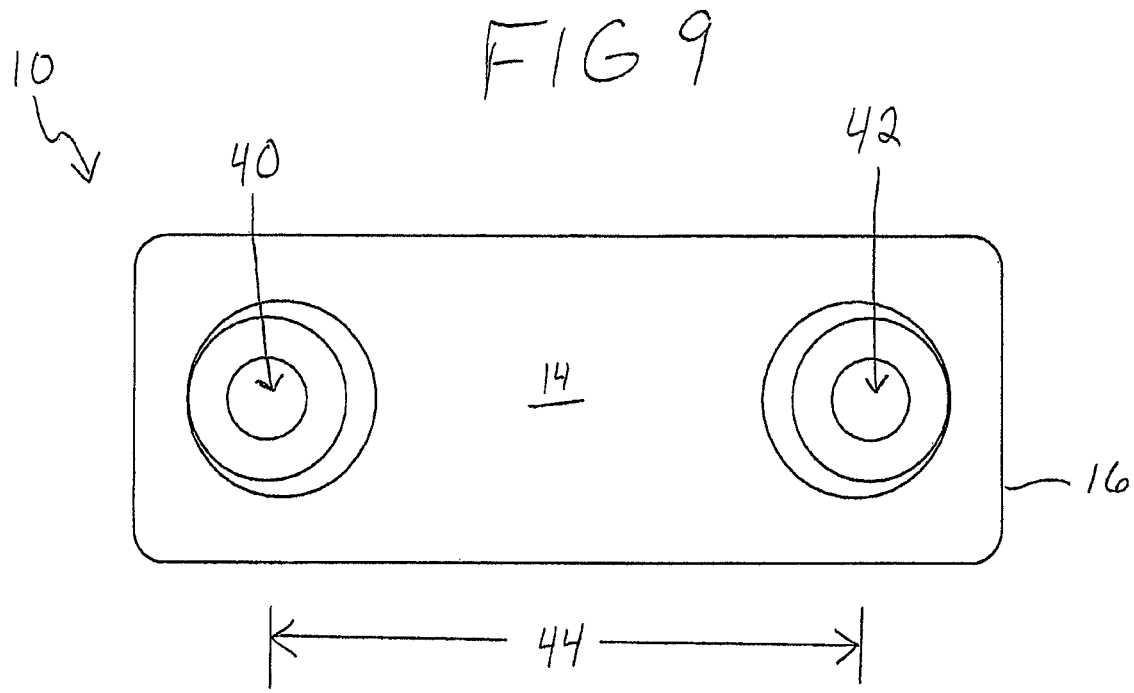
FIG. 9 is a first end view of an embodiment of the vee manifold.
Figure 10:
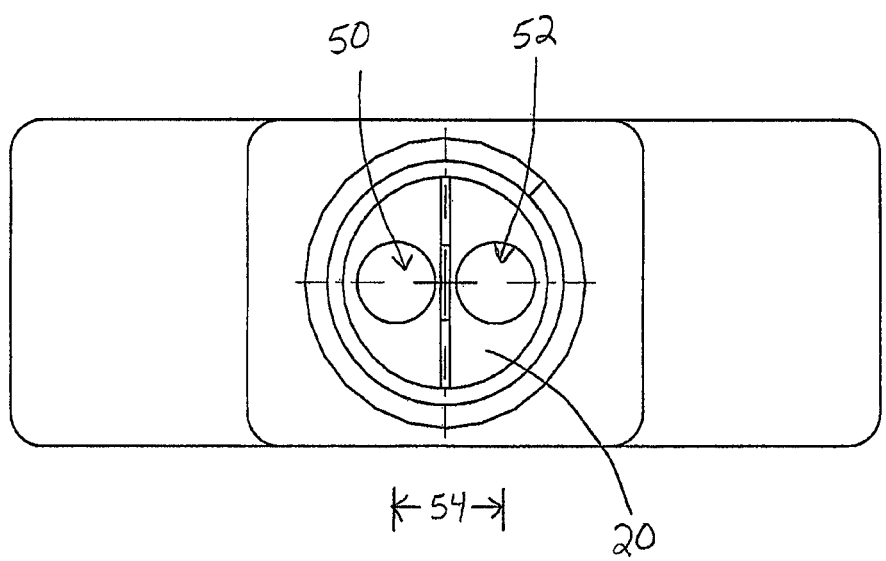
FIG. 10 is a second end view of an embodiment of the vee manifold.

Vee manifold 10 has a plurality of inlets or apertures 12 on a top or first side 14 of a block 16. For example, first side 14 of block 16 includes a first side first aperture 40 and a first side second aperture 42. Referring to FIG. 9, first side second aperture 42 is spaced a first distance 44 from first side first aperture 40. Each of the inlets 12 may be independently configured as first connection means. The block 16 has a bottom or second side 20 opposite top side 14. Bottom side 20 has an outlet portion or apertures 22. For example, second side 20 of block 16 includes a second side first aperture 50 and a second side second aperture 52. Referring to FIG. 10, second side second aperture 52 is spaced a second distance 54 from second side first aperture 50. In one embodiment, referring to FIG. 6, second side second aperture 52 and second side first aperture 50 merge but are still spaced a second distance 54 from one another as shown in FIG. 6. In one embodiment, first distance 44 is greater than second distance 54 as shown in FIGS. 9 and 10. The outlet portion 22 may be configured as second connection means. The block 16 between each of the plurality of inlets 12 and the outlet portion 22 defines straight, cylindrical channels 30. For example, a first channel 60 defining a first channel longitudinal axis 62 extends from first side first aperture 40 to second side first aperture 50. In one embodiment, the first channel longitudinal axis 62 is linear. Additionally, a second channel 70 defining a second channel longitudinal axis 72 extends from first side second aperture 42 to second side second aperture 52. In one embodiment, the second channel longitudinal axis 72 is linear.

In the embodiment illustrated in FIGS. 1-10, first side 14 and second side 20 of block 16 are generally parallel to one another and the first channel longitudinal axis 62 and the second channel longitudinal axis 72 are not perpendicular to first side 14 or second side 20 of block 16. In one embodiment, the first channel longitudinal axis 62 and the second channel longitudinal axis 72 are oblique to first side 14 and second side 20, i.e., the first channel longitudinal axis 62 and the second channel longitudinal axis 72 are neither parallel nor perpendicular to first side 14 and second side 20.

The inlets 12 may be first connection means to attach hoses, tubing, piping, nipples, valves, or other apparatus, such as hoses 90 (FIG. 7), by any fluid connection means known in the industry. Connection means include, but are not limited to, tapered walls for a friction fit, threads, quick connects, compression fittings, flare fittings, flange fittings, mechanical fittings, Luer locks, welding, soldering, and/or brazing. Each of the inlets may utilize the same or different connection means. Preferably, the connection means for inlets 12 are threads 24. A preferred embodiment has two inlets 12. In other embodiments, the vee manifold 10 has three, four, five or more inlets 12. If one or more inlets 12 are not being utilized, they may be capped by any capping means, such as a plug.

Block 16 may be made of any suitable material for the fluids. Materials for construction of block 16 may comprise, but not limited to, carbon steel, low temperature service carbon steel, stainless steel, non-ferrous metal alloys such as Inconel, Incoloy, and Cupro-nickel, non-metallic materials such as acrylonitrile butadiene styrene (ABS) polymer, glass fiber reinforced epoxy (GRE), polyvinyl chloride (PVC), chlorinated polyvinyl chloride (CPVC), ultra-high-molecular-weight polypropylene (UHMW), high density polyethylene (HDPE), tempered glass, perfluorinated polymers such as Teflon, chrome-molybdenum steel, aluminum, bronze, brass and copper. However, any other material may be used that is compatible with the materials to be used in the system. Preferably, block 16 is made of a polymer. More preferably, block 16 is made of UHMW. In some embodiments, means for heating vee manifold 10 are provided. Heating means include any means known in the industry for heating parts, including, but not limited to, electrical resistance or a fluid jacket.

The outlet portion 22 has second connection means to attach an outlet hose, spray nozzle, static mixing tip, such as static mixing tip 92 or spray nozzle 94 (FIGS. 7-8B), or other tubing, piping, nipples, valves, or other apparatus by any fluid connection means known in the industry. Connection means include, but are not limited to, tapered walls for a friction fit, threads, quick connects, compression fittings, flare fittings, flange fittings, mechanical fittings, Luer locks, welding, soldering, and/or brazing. Preferably, the connection means for the outlet portion 22 are threads 24 for connecting hoses and mixing tips (see FIG. 3).

The straight, cylindrical channels 30 in the block 16 are generally straight, have a generally circular cross-section, of a generally constant diameter. The cylindrical channels 30 have an inlet opening 36 and an outlet opening 38. Preferably, inlet openings 36 open into female inlets 32 as shown in FIG. 3. In other preferred embodiments, the inlet openings 36 open into male inlets 34. The cylindrical channels 30 in a block 16 may have the same diameter, or vary individually in diameter as needed by the application governed by the material characteristics of the fluids. Each of the outlet openings 38 open into the outlet portion 22. Preferably, as illustrated in FIGS. 1-3, the outlet openings 38 of each of the cylindrical channels 30 are distinct, the orifices are separate and do not communicate with each other. In other embodiments, FIG. 6, the outlet openings 38 of two or more cylindrical channels 30 may merge as a single outlet opening 38.

In use, a plurality of fluid materials enter the vee manifold 10 through inlets 12, the materials pass through the vee manifold 10. For example, referring to FIG. 7, a first substance 80 is movable through first channel 60 and a second substance 82 is movable through second channel 70. In some embodiments, first substance 80 and second substance 82 are different substances. When fluid material flow is stopped, a chemical reaction or physical change of the fluid materials may cause hardening to form a solid mass as in the prior art wye manifolds. The solid mass may form in the cylindrical channels 30 to form a cylindrical shaped clog. The cylindrical shaped clog may typically be extruded by increasing pressure through the inlets 12 restoring normal flow. As an alternative to increasing pressure, a straight drill bit may be introduced into the cylindrical channels 30 for the length of the block 16 to remove the cylindrical shaped clog.

A feature of the vee manifold 10 is that each cylindrical channel 30 is generally straight, and preferably at an angle relative to other channels 30 from the inlet openings 36 to the outlet openings 38. This straight pathway is simple and effective. If the flowable liquids used in the vee manifold 10 harden through chemical or physical changes, the solids formed have the straight sides of the straight cylindrical channels 30 act as a mold to form a hardened clog with a shape that is cylindrical. The cylindrical shaped clog can often be extruded by increasing the pressure on the upstream liquid. Once the clog is extruded normal flow is restored. The hardened mass can often be extruded out through the outlet openings 38 without resorting to other mechanical means.

If increased pressure will not extrude the hardened material out the outlet openings 38 then the clogs can be removed by mechanical means. As the flow path through the cylindrical channels 30 is straight, mechanical means such as a standard straight drill bit can be inserted into the outlet opening 38 and run all the way up through the clogged material in the cylindrical channels 30 to restore the functionality of the vee manifold 10. Ordinarily, the supply hoses do not need to be disconnected and an expensive mess is avoided.

For example, referring to FIG. 7, a clog 96 formed within a vee manifold 10 of the present disclosure can be easily cleaned. To clean a clog 96, a user only needs to remove static mixing tip 92 from second side 20 of vee manifold 10. With static mixing tip 92 removed, a tool such as drill bit 98 can be inserted into first channel 60 and/or second channel 70 to quickly and easily clean the channels 60 and 70. Because first channel longitudinal axis 62 and second channel longitudinal axis 72 are linear as shown in FIG. 7, the drill bit 98 only needs to enter each channel 60 and 70 a single time to completely and efficiently clear out any clogs 96. Once the channels 60 and 70 are cleaned, static mixing tip 92 is secured to second side 20 of vee manifold 10.

Figure 11:
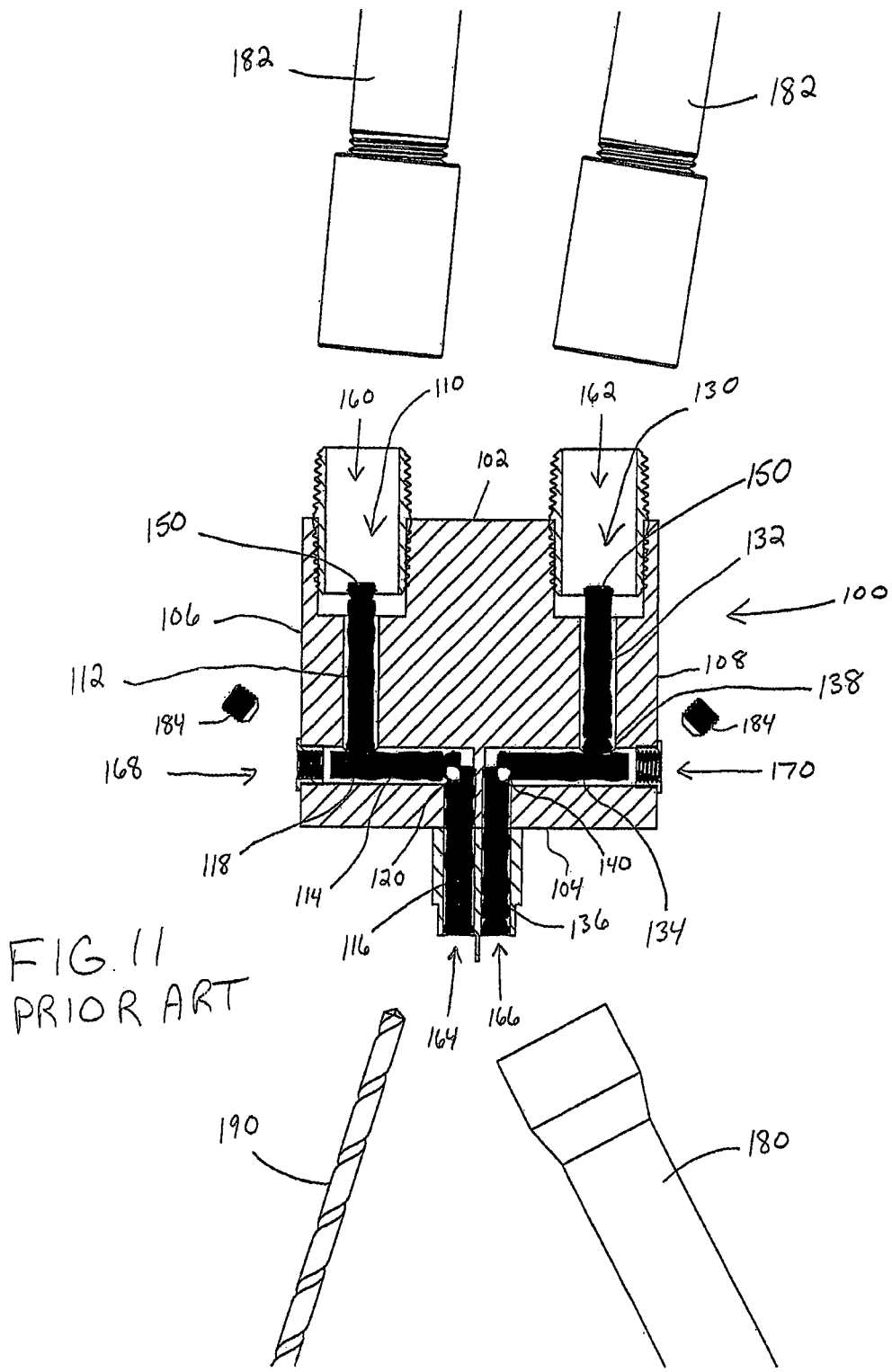
FIG. 11 is a cross-sectional view of a prior art manifold.

Disadvantageously, referring to FIG. 11, a clog 150 formed within a prior art manifold 100 is difficult to clean. Prior art manifold 100 includes first side 102 defining first input 160 and second input 162, second side 104 defining third input 164 and fourth input 166, third side 106 defining fifth input 168, and fourth side 108 defining sixth input 170. A first angled channel 110 includes a first channel portion 112, a second channel portion 114 located perpendicular to first channel portion 112, and a third channel portion 116 located perpendicular to second channel portion 114. First and second channel portions 112 and 114 are connected by a first elbow or first ninety-degree turn 118 and second and third channel portions 114 and 116 are connected by a second elbow or second-ninety degree turn 120 as shown in FIG. 11. A second angled channel 130 includes a first channel portion 132, a second channel portion 134 located perpendicular to first channel portion 132, and a third channel portion 136 located perpendicular to second channel portion 134. First and second channel portions 132 and 134 are connected by a first elbow or first ninety-degree turn 138 and second and third channel portions 134 and 136 are connected by a second elbow or second-ninety degree turn 140 as shown in FIG. 11. As discussed previously, to clean a clog 150 from a prior art manifold 100, a user needs to remove a downstream plumbing component 180, liquid supply lines 182, and side set screws 184 as shown in FIG. 11. Next, a user must plug liquid supply lines 182 to prevent undesired drainage. Only after all these components are removed and plugged may a tool such as drill bit 190 be inserted. However, to clean first angled channel 110, a user must insert the drill bit 190 into first input 160 to clear out the clog 150 in first channel portion 112. Next, the user must insert the drill bit 190 into third input 164 to clear out the clog 150 in third channel portion 116. Next, the user must insert the drill bit 190 into fifth input 168 to clear out the clog 150 in second channel portion 114. To clean second angled channel 130, a user must insert the drill bit 190 into second input 162 to clear out the clog 150 in first channel portion 132. Next, the user must insert the drill bit 190 into fourth input 166 to clear out the clog 150 in third channel portion 136. Next, the user must insert the drill bit 190 into sixth input 170 to clear out the clog 150 in second channel portion 134. After all six of these inputs are cleaned, then a user must reinstall side set screws 184, remove the plugs in liquid supply lines 182, reconnect the liquid supply lines 182, and reconnect downstream plumbing component 180. The process to clean a prior art manifold 100 is very time consuming and complicated.

Where mixing occurs downstream of the vee manifold 10, an efficient method of preventing overnight hardening in the vee manifold 10 is to do nothing as material downstream acts as a seal of the vee manifold 10.

Comparative Example

A white lap adhesive is commonly used in the roofing industry to seal membranes. The white lap adhesive involves the mixing of a first material comprising of polyurethane polymer and an isocyanate, and a second material comprising a polyol and polypropylene glycol. Common industry practice utilizes wye manifolds, as shown in U.S. patent application publication 2012/0012054 A1 FIG. 5, for this application. Chemical reaction within wye manifolds can create a solid clog requiring one hour of down time to restore the wye manifolds to production. A preferred embodiment of the vee manifold 10 made of UHMW, having two inlets 12, two cylindrical channels 30, individual outlet openings 38 and a mixing tip, was used with the white lap adhesive (FIGS. 1-3) and similar clogs cleared in about 15 seconds upon applying upstream pressure from the fluids.

In the foregoing Detailed Description, various features are grouped together in a single embodiment to streamline the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Further, although elements of the described aspects and/or embodiments may be described or claimed in the singular, the plural is contemplated unless limitation to the singular is explicitly stated. The following claims are hereby incorporated into the Detailed Description, with each claim standing on its own as a separate embodiment.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A manifold for a first chemical substance and a second chemical substance to travel therethrough, the first chemical substance is a first part of a multiple component adhesive and the second chemical substance is a second part of the multiple component adhesive, the first chemical substance and the second chemical substance are configured to cure upon mixing to form a third homogeneous chemical substance, the manifold comprising:
a block having a first side and a second side, the block having a vee-shape;
a first channel extending from the first side to the second side, the first channel defining a first channel longitudinal axis, the first channel longitudinal axis being linear; and
a second channel extending from the first side to the second side, the second channel defining a second channel longitudinal axis, the second channel longitudinal axis being linear,
wherein the first channel and the second channel together form a vee-shape,
wherein the first side of the block includes a first threaded connection portion and the second side of the block includes a second threaded connection portion,
wherein a portion of the first channel is within the second threaded connection portion and a portion of the second channel is within the second threaded connection portion,
wherein the second threaded connection portion defines a second threaded connection portion longitudinal axis, wherein the portion of the first channel within the second threaded connection portion is oblique to the second threaded connection portion longitudinal axis, and wherein the portion of the second channel within the second threaded connection portion is oblique to the second threaded connection portion longitudinal axis, and
wherein the first threaded connection portion defines a first threaded connection portion longitudinal axis, and wherein the first threaded connection portion longitudinal axis is oblique to the second threaded connection portion longitudinal axis.

2. The manifold of claim 1, wherein the first channel and the second channel are inclined toward each other as the first channel and the second channel extend from the first side of the block to the second side of the block.

3. The manifold of claim 1, wherein the first side of the block has a first width and the second side of the block has a second width, the first width greater than the second width.

4. The manifold of claim 1, wherein the first channel has a uniform diameter.

5. The manifold of claim 1, wherein the second channel has a uniform diameter.

6. The manifold of claim 1, wherein the first channel and the second channel intersect at a point outside of the block.

7. The manifold of claim 1, further comprising:
wherein the first threaded connection portion is disposed at a first portion of the first side of the block;
a third threaded connection portion disposed at a second portion of the first side of the block; and
wherein the second threaded connection portion is disposed at a first portion of the second side of the block.

8. The manifold of claim 7, wherein the first threaded connection portion, the second threaded connection portion, and the third threaded connection portion comprise a ⅞ inch thread diameter.

9. The manifold of claim 1, further comprising an exit portion of the manifold configured for the first chemical substance and the second chemical substance to travel therethrough, the second threaded connection portion comprises an external threaded connection portion configured to interlock with an internal threaded connection portion of a multiple component adhesive mixing tip.

10. The manifold of claim 1, wherein the first channel and the second channel are coplanar.

11. A manifold for a first chemical substance and a second chemical substance to travel therethrough, the first chemical substance is a first part of a multiple component adhesive and the second chemical substance is a second part of the multiple component adhesive, the first chemical substance and the second chemical substance are configured to cure upon mixing to form a third homogeneous chemical substance, the manifold comprising:
a block having a first side and a second side, the block having a vee-shape;
a first channel extending from the first side to the second side, the first channel defining a first channel longitudinal axis, the first channel longitudinal axis being linear; and
a second channel extending from the first side to the second side, the second channel defining a second channel longitudinal axis, the second channel longitudinal axis being linear,
wherein the first channel and the second channel together form a vee-shape,
wherein the block has a stepped surface adjacent the second side,
wherein the first side of the block includes a first threaded connection portion and the second side of the block includes a second threaded connection portion,
wherein a portion of the first channel is within the second threaded connection portion and a portion of the second channel is within the second threaded connection portion,
wherein the second threaded connection portion defines a second threaded connection portion longitudinal axis, wherein the portion of the first channel within the second threaded connection portion is oblique to the second threaded connection portion longitudinal axis, and wherein the portion of the second channel within the second threaded connection portion is oblique to the second threaded connection portion longitudinal axis, and
wherein the first threaded connection portion defines a first threaded connection portion longitudinal axis, and wherein the first threaded connection portion longitudinal axis is oblique to the second threaded connection portion longitudinal axis.

12. The manifold of claim 11, wherein the first channel and the second channel are inclined toward each other as the first channel and the second channel extend from the first side of the block to the second side of the block.

13. The manifold of claim 11, wherein the first side of the block has a first width and the second side of the block has a second width, the first width greater than the second width.

14. The manifold of claim 11, wherein the first channel has a uniform diameter.

15. The manifold of claim 11, wherein the second channel has a uniform diameter.

16. The manifold of claim 11, wherein the first channel and the second channel intersect at a point outside of the block.

17. The manifold of claim 11, further comprising:
wherein the first threaded connection portion is disposed at a first portion of the first side of the block;
a third threaded connection portion disposed at a second portion of the first side of the block; and
wherein the second threaded connection portion is disposed at a first portion of the second side of the block.

18. The manifold of claim 17, wherein the first threaded connection portion, the second threaded connection portion, and the third threaded connection portion comprise a ⅞ inch thread diameter.

19. The manifold of claim 11, wherein the first channel and the second channel are coplanar.

20. The manifold of claim 11, wherein the second threaded connection portion comprises an external threaded connection portion configured to interlock with an internal threaded connection portion of a multiple component adhesive mixing tip.

* * * * *